United States Patent
Berberich

(10) Patent No.: US 8,529,593 B2
(45) Date of Patent: Sep. 10, 2013

(54) MEDICAL INSTRUMENT FOR CUTTING TISSUE

(75) Inventor: Sascha Berberich, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 122 days.

(21) Appl. No.: 11/782,304

(22) Filed: Jul. 24, 2007

(65) Prior Publication Data

US 2008/0021488 A1  Jan. 24, 2008

(30) Foreign Application Priority Data

Jul. 24, 2006  (DE) .................. 10 2006 034 756

(51) Int. Cl.
*A61B 17/32* (2006.01)

(52) U.S. Cl.
USPC .......................................... 606/180; 606/159

(58) Field of Classification Search
USPC ............. 606/79–85, 170, 180, 171, 172, 159, 606/167
See application file for complete search history.

(56) References Cited

U.S. PATENT DOCUMENTS

| | | | |
|---|---|---|---|
| 4,811,734 A | | 3/1989 | McGurk-Burleson et al. |
| 4,834,729 A | * | 5/1989 | Sjostrom ...................... 606/170 |
| 4,844,088 A | | 7/1989 | Kambin |
| 5,084,052 A | * | 1/1992 | Jacobs ............................ 606/79 |
| 5,112,299 A | * | 5/1992 | Pascaloff ........................ 604/22 |
| 5,474,532 A | | 12/1995 | Steppe |
| 5,489,291 A | | 2/1996 | Wiley |
| 5,527,331 A | | 6/1996 | Kresch et al. |
| 5,741,287 A | * | 4/1998 | Alden et al. .................. 606/170 |
| 5,857,995 A | * | 1/1999 | Thomas et al. ................. 604/22 |
| 6,053,923 A | | 4/2000 | Veca et al. |
| 6,342,061 B1 | * | 1/2002 | Kauker et al. ................ 606/180 |
| 6,610,059 B1 | | 8/2003 | West, Jr. |
| 2007/0282361 A1 | | 12/2007 | Da Rold et al. |

FOREIGN PATENT DOCUMENTS

WO  2006011119 A1  2/2006

OTHER PUBLICATIONS

*Ex parte* Robson, Appeal 2008-006370, (BPAI, Apr. 30, 2010), available at http://e-foia.uspto.gov/Foia/ReterivePdf?system=BPAI&flNm=fd2008006370-04-30-2010-1 (last visited on Feb. 1, 2013).*
European Search Report, Nov. 5, 2007, 4 pages.

\* cited by examiner

*Primary Examiner* — Thomas McEvoy
(74) *Attorney, Agent, or Firm* — St. Onge Steward Johnston & Reens LLC

(57) ABSTRACT

A medical instrument for cutting tissue having a tubular outer shaft which, in the area of its distal end, has at least one window with at least one blade, and further comprises a tubular inner shaft which is rotatable about a longitudinal axis, is received in the outer shaft and has, at its distal end, a cutting element which is arranged in the area of the at least one window of the outer shaft and is provided with several circumferentially arranged openings, each of the openings of the cutting element having at least one blade which, when the cutting element is moved in rotation, cooperates in a cutting action with the at least one blade of the outer shaft. It is proposed that at least some of the openings of the cutting element should have different widths, seen in a circumferential direction.

2 Claims, 4 Drawing Sheets

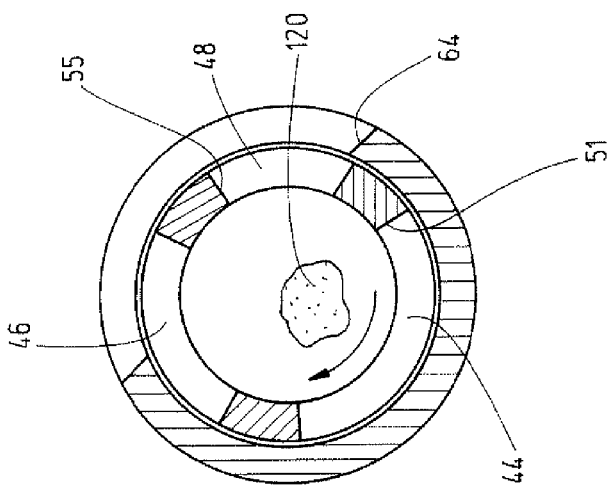
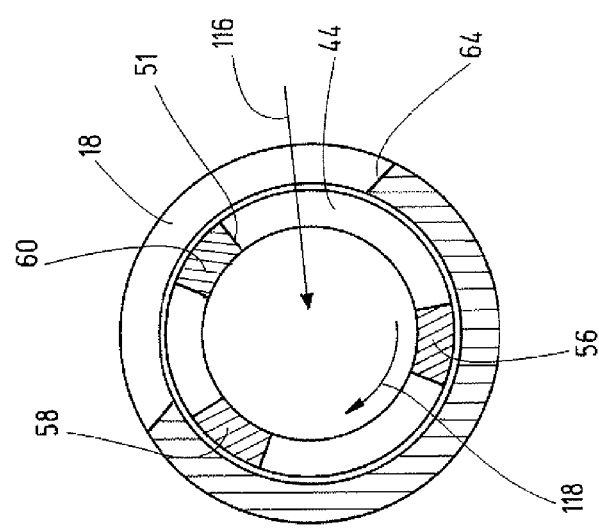
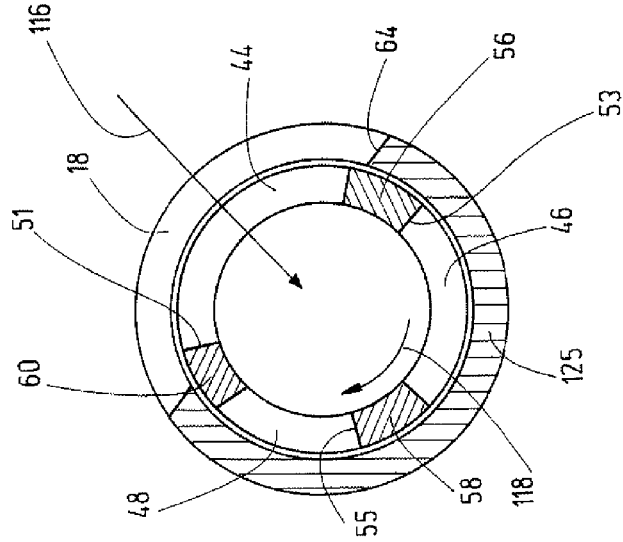

MEDICAL INSTRUMENT FOR CUTTING TISSUE

BACKGROUND OF THE INVENTION

The invention relates to a medical instrument for cutting tissue.

An instrument of this kind is known from U.S. Pat. No. 5,489,291.

Such instruments are used in minimally invasive surgery for detaching tissue in the human or animal body. To do so, a distal end of a shaft is guided to the operating site where the tissue that is to be detached is situated. To detach the tissue, a cutting element is moved in rotation by means of an external or internal motor. During the rotation, a blade formed on the cutting element cooperates in a cutting action with an edge of a window in the shaft, which edge is designed as a blade. The blade of the cutting element passes the blade of the window upon each revolution. To ensure that the tissue to be detached can be brought between the interacting blades, the shaft of such instruments is connected to a suction source. The suction effect of the suction source reaches through the inner hollow space of the shaft as far as the window, in order to suck the tissue to be detached through the window and into the shaft, such that the blades can sever the tissue. The detached tissue is sucked through the shaft by the partial vacuum.

The instrument known from U.S. Pat. No. 5,489,291 mentioned above comprises an outer shaft, which is beveled at its distal end. A tubular rotatable inner shaft, at whose distal end a cutting element is formed, is received in the outer shaft. The cutting element has several openings which, seen in a circumferential direction, are of the same width. Each of the openings has a blade.

The tissue to be detached is sucked into one of the openings of the cutting element rotating in the outer shaft. The tissue is then severed by means of the blade-type edge of the cutting element opening, into which the tissue to be detached is sucked, running past the leading rotating edge of the pointed part of the outer shaft. After the tissue has been detached, it is sucked through the inner shaft to the proximal end of the instrument.

Since the width of the several openings of the cutting element is the same, seen in a circumferential direction, it is found that only tissue whose width corresponds approximately to the width of the openings of the cutting element can be effectively and efficiently sucked into the openings and thus be detached. Tissue that is appreciably larger than the openings of the cutting element is either not sucked at all, or sucked only partially, into the openings of the cutting element. It has been found that, for a cutting element of a defined size, there is likewise a defined size of the tissue that can be effectively detached. Particularly for large tissue parts, multiple cuts are needed, which lead to fraying and leaves behind shreds of tissue.

Therefore, the disadvantage of the known instrument is that the tissue to be detached cannot in fact be detached very efficiently and satisfactorily.

It is therefore an object of the present invention to develop an instrument of the type mentioned at the outset in such a way that the cutting performance or cutting efficacy is improved.

SUMMARY OF THE INVENTION

This object is achieved by a medical instrument for cutting tissue comprising a tubular shaft having in an area of its distal end at least one window, said window having at least one blade, a tubular inner shaft being rotatable about a longitudinal axis, that tubular inner shaft is received within said outer shaft, said tubular inner shaft having at a distal end thereof a cutting element which is arranged in an area of said at least one window of said outer shaft, said cutting element having several circumferentially arranged openings, each of said openings of said cutting element having at least one blade which, when said cutting element is moved in rotation within said outer shaft cooperates in a cutting action with said at least one blade of said outer shaft, wherein at least some of said openings of said cutting element have different widths, seen in a circumferential direction of said cutting element.

This measure has, among other things, the considerable advantage that, since at least some of the openings of the cutting element have different widths, seen in a circumferential direction, it is possible for different sizes of tissue fragments to be sucked in. The term at least some means that at least two different widths are present. It is possible to provide groups of openings with identical width, but the width changes from group to group.

During a complete revolution of the cutting element, different sizes of tissue fragments can be sucked into the openings of the rotating cutting element, which openings have different widths seen in a circumferential direction, and, as a result, different sizes of tissue fragments can be efficiently detached. Thus, during one revolution, several different widths of openings are available for taking up correspondingly different sizes of tissue fragments.

It was recognized that the detached tissue is cut up into small pieces, due to the different width openings, thus avoiding clogging of the cutting element. This also leads to an improved cutting performance or cutting action.

In another embodiment of the invention, each of the openings has a different width, seen in a circumferential direction.

This measure has the advantage that, during a complete revolution of the cutting element, each cutting process takes place with different sizes of tissue fragments which can be sucked in and detached. This results in a very high degree of efficiency of the cutting performance and cutting action.

In another embodiment of the invention, the cutting element has three openings.

This measure has the advantage that, with this number of openings, there is the possibility of producing a cutting element in which the width of the openings of the cutting element, seen in a circumferential direction, differs considerably. This has the effect that, during a complete revolution of the cutting element, three cutting processes can take place in which tissue fragments of considerably different sizes can be effectively detached.

In another embodiment of the invention, the at least one window of the outer shaft, seen in a circumferential direction, is wider than the largest opening of the cutting element.

This measure has the advantage that the at least one window of the outer shaft is never fully closed during a complete revolution of the cutting element. This means that the suction effect through the window is not interrupted, with the result that the detached tissue can be sucked in continuously.

While tissue that has been sucked in is being detached by the cutting element, other tissue that is to be detached is already being sucked in at the same time through the window into another opening of the cutting element and can be detached in the next cutting process. The tissue can be efficiently detached in this way.

In another embodiment of the invention, the openings are each separated by a web.

This measure has the advantage that a cutting element with circumferentially offset openings can be produced in a simple way through such embodiments. A cutting element designed in this way has a particularly high degree of stability.

In another embodiment of the invention, the webs, seen in a circumferential direction, have a smaller width than the at least one window of the outer shaft.

This measure has the advantage that the suction effect through the window of the outer shaft is uninterrupted throughout the entire work cycle of the cutting element. By means of the fact that the tissue to be detached is permanently sucked into the outer shaft in connection with several cutting processes during a complete revolution of the cutting element, a high cutting performance of the instrument according to the invention is achieved.

In another embodiment of the invention, the outer shaft has a single window.

This measure has the advantage that an outer shaft designed in this way can be laterally guided, with particular precision, toward the tissue that is to be detached.

In another embodiment of the invention, the outer shaft has several circumferentially offset windows.

This measure has the advantage that the cutting performance of the instrument according to the invention can be further improved. An outer shaft with several windows can be combined with a cutting element with several openings, in order to still further increase the cutting performance of the instrument according to the invention. This has the effect that a substantially greater number of blades are used, and more tissue can therefore be detached in a short time.

In another embodiment of the invention, the windows of the outer shaft have the same geometry as the openings of the cutting element received in this outer shaft.

This measure has the advantage that the cutting performance is improved still further. By means of such a combination, the blades work more efficiently, as a consequence of which more tissue can be detached more quickly.

Such an embodiment of the instrument according to the invention also has the effect that clogging of the cutting element is avoided, since detached tissue parts or caught tissue parts are divided up into several small fragments.

It will be appreciated that the aforementioned features and those still to be explained below can be used not only in the cited combinations, but also in other combinations, without departing from the scope of the present invention.

BRIEF DESCRIPTION OF THE DRAWINGS

The invention is described and explained in more detail below on the basis of a chosen illustrative embodiment and with reference to the drawings, in which:

FIG. 6 shows a cross section along the line VI-VI in FIG. 1, FIG. 7 is a cross section, corresponding to FIG. 6, and shows the cutting element in a different position of rotation compared to FIG. 6, and FIG. 8 is a cross section, corresponding to FIG. 6, and shows the cutting element in a different position of rotation compared to FIG. 7.

DETAILED DESCRIPTION OF PREFERRED EMBODIMENTS

Figure 1:
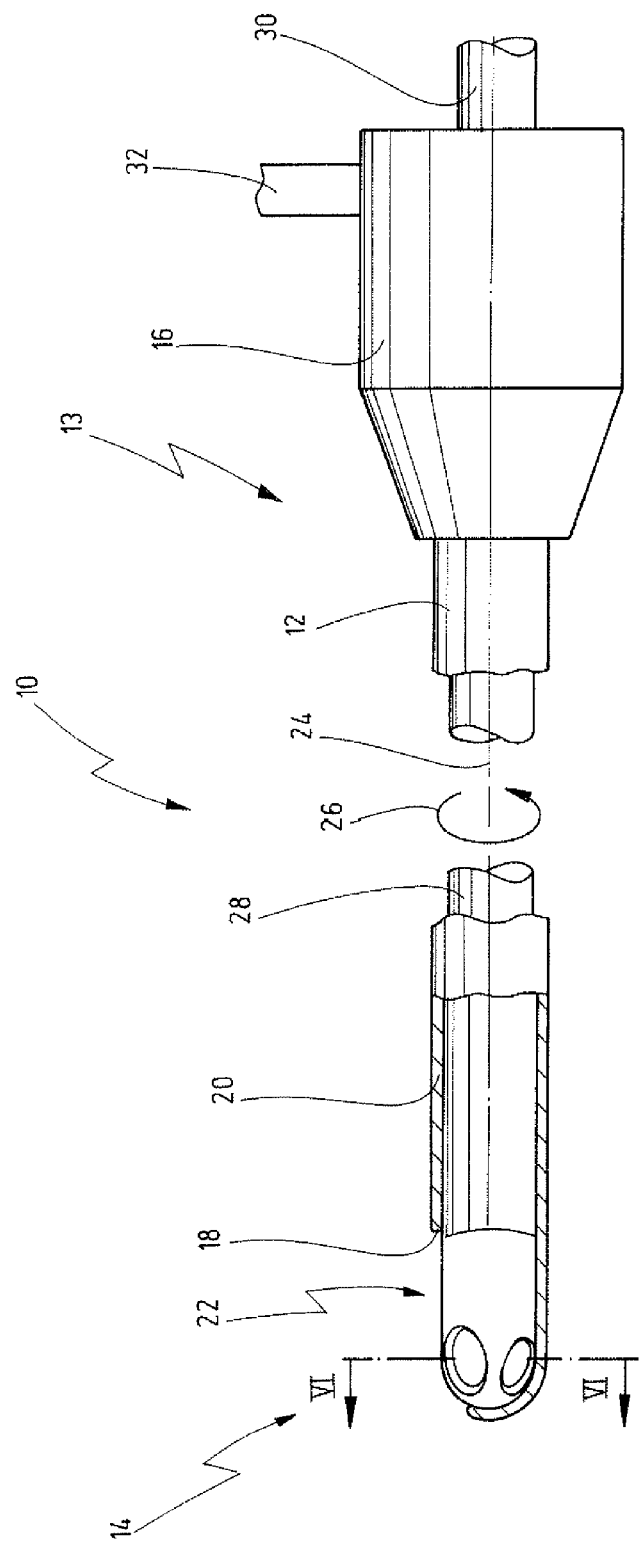
FIG. 1 shows a side view, in partial cross section, of a medical instrument for cutting tissue.

A medical instrument shown in the figures, and used for cutting tissue, is designated in its entirety by reference number 10.

The medical instrument 10 comprises a tubular outer shaft 12 which, at its proximal end 13, is connected to a housing 16.

In its rounded and closed distal end 14, the outer shaft 12 comprises a window 18. The window 18 is formed by means of a circumferentially and axially limited opening of approximately triangular shape being made in a wall 20 of the outer shaft 12, as can be seen from FIG. 1 in conjunction with FIG. 3.

In the area of the window 18, a cutting element 22 is arranged within the outer shaft 12. The cutting element 22 is received in the outer shaft 12 in such a way as to be able to rotate about a longitudinal axis 24 of the medical instrument 10, and it can accordingly be moved in rotation in the stationary outer shaft 12 in the direction indicated by an arrow 26.

The cutting element 22 is arranged on and integrally connected to the distal end 14 of a tubular inner shaft 28, which is connected to a drive shaft 30 at the proximal end 13. The drive shaft 30 is moved in rotation according to the arrow 26 by means of a motor (not shown), and the rotary movement of the drive shaft 30 is transmitted via the inner shaft 28 to the cutting element 22 integrally connected to the latter.

Moreover, the instrument 10 can be connected to a suction source (not shown) whose suction line can be attached to a nozzle 32 of the housing 16. With the suction source connected up and switched on, a suction current forms through the inner shaft 28 around the cutting element 22 to as far as the window 18 and is directed from the window 18 to the nozzle 32.

Figure 2:
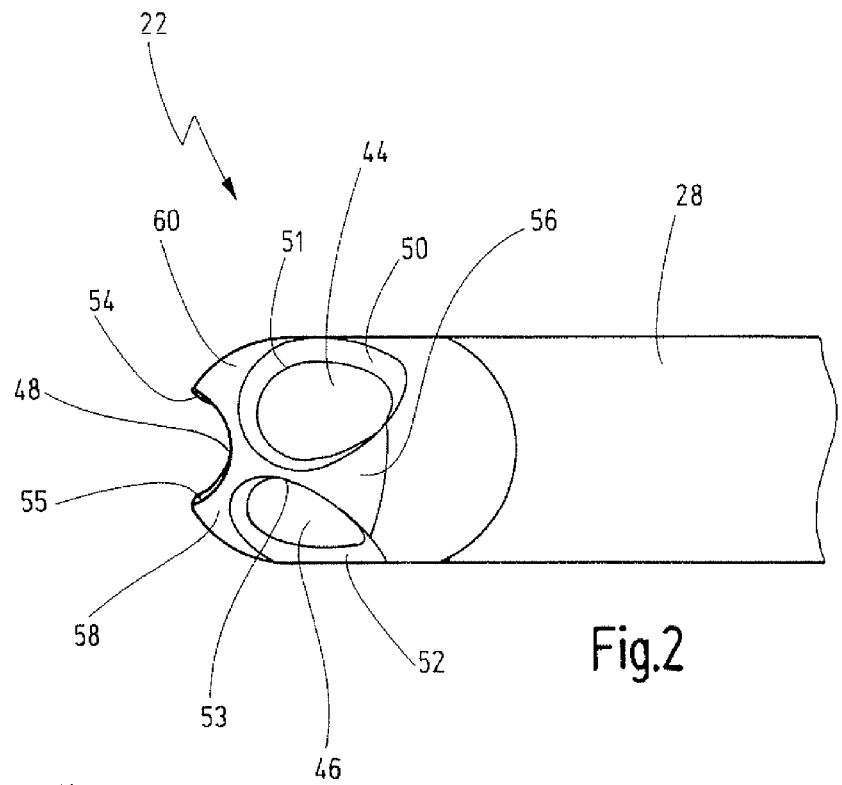
FIG. 2 shows an enlarged view of the distal end portion of the cutting element from FIG. 1.

As can be seen from the enlarged view in FIG. 2, the cutting element 22 has three circumferentially arranged openings 44, 46, 48 which, seen in a circumferential direction, have different widths. The opening 44 has the greatest width, while the opening 48 has the smallest.

The openings 44, 46, 48 are separated from one another by three webs 56, 58, 60.

The openings 44, 46, 48 each have an edge 50, 52, 54. Each edge 50, 52, 54 is designed as a blade 51, 53, 55.

Figure 3:
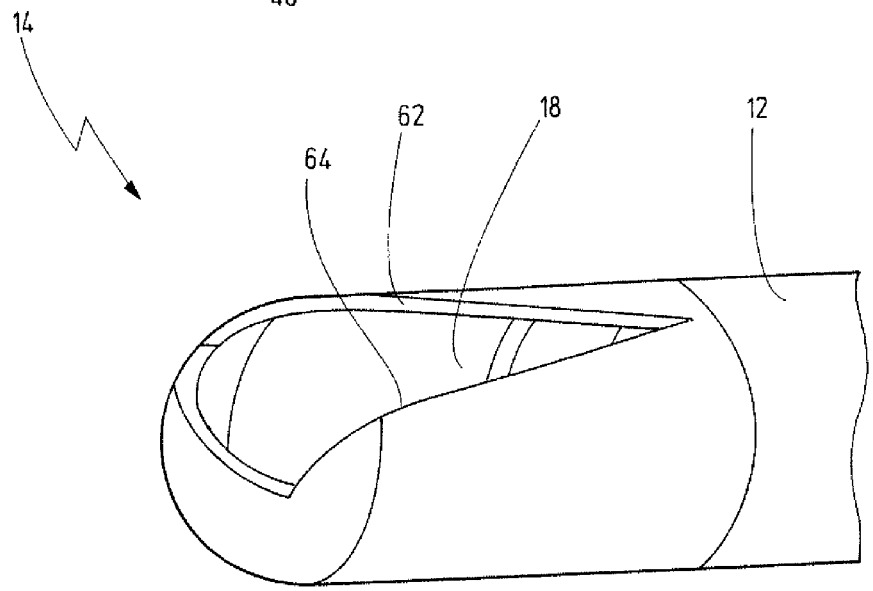
FIG. 3 shows an enlarged view of the distal end of the outer shaft from FIG. 1.

FIG. 3 shows an enlarged view of the distal end 14 of the outer shaft 12 from FIG. 1.

The window 18 arranged at the distal end 14 of the outer shaft 12 has an edge 62, which is designed as a blade 64.

Figure 4:
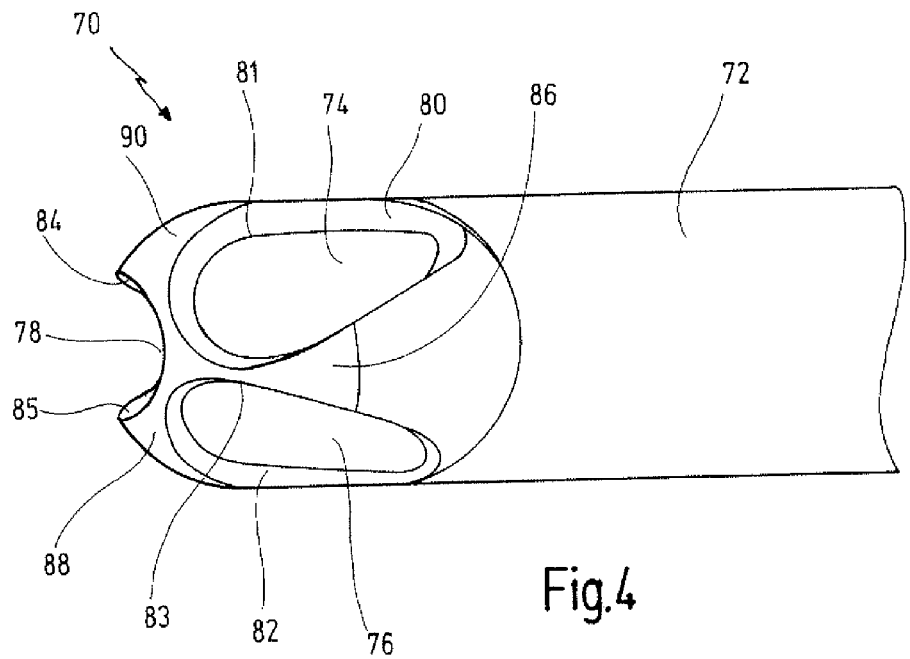
FIG. 4 shows another illustrative embodiment of a cutting element in a view corresponding to FIG. 2.

FIG. 4 shows another illustrative embodiment of a cutting element 70, which differs from the illustrative embodiment shown in FIG. 2 in terms of the length of the three openings.

In the illustrative embodiment shown in FIG. 4, the cutting element 70 also has three openings 74, 76, 78 that are offset about the circumference and are separated from one another by three webs 86, 88, 90. The openings 74, 76, 78 also each have an edge 80, 82, 84 designed as a blade 81, 83, 85.

Compared to the illustrative embodiment in FIG. 2, it will be seen that the axial length of the openings 74, 76, 78 is greater than the length of the openings 44, 46, 48.

Figure 5:
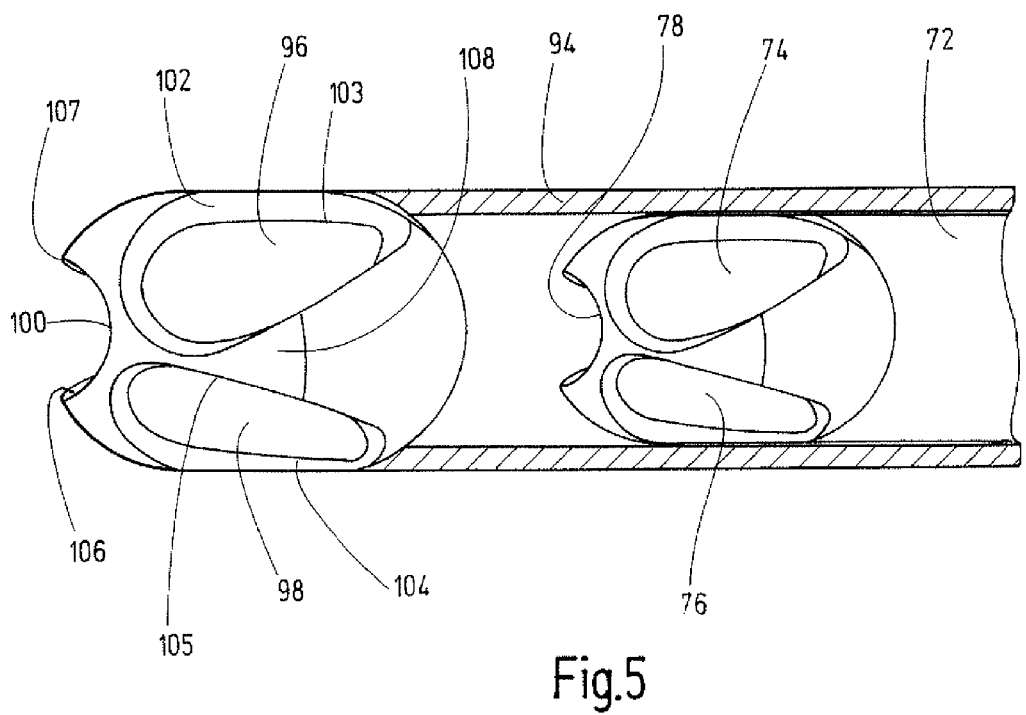
FIG. 5 shows the illustrative embodiment of the cutting element from FIG. 4, with the cutting element now having been pushed into an outer shaft whose windows have the same geometry as the openings of this cutting element.

FIG. 5 shows a situation in which the cutting element 70 from FIG. 4 is pushed into an outer shaft 94, the distal end 92 of which has three windows 96, 98, 100 that have the same geometry and shape as the three openings 74, 76, 78 of the cutting element 70.

The circumferentially arranged windows 96, 98, 100 are separated from one another by three webs 108, 110, 112.

The windows 96, 98, 100 also each have an edge 102, 104, 106 designed as a blade 103, 105, 107.

The use of the medical instrument 10 from FIG. 1 will be briefly explained with reference to FIGS. 6 to 8.

FIG. 6 shows three openings 44, 46, 48 of the cutting element 22, which are separated from one another by three webs 56, 58, 60.

As the cutting element 22 revolves in the outer shaft 12 in the direction of rotation indicated by the arrow 118, the blades 51, 53, 55 cooperate in a cutting action with the blade 64, which is formed on the lateral edge 62 of the window 18 of the outer shaft 12.

For cutting or detaching tissue, indicated by the arrow 116, the instrument 10, in the area of the window 18, is placed against the tissue, the cutting element 22 is driven in rotation, and the suction source is used to create a suction current through the inner shaft 28 as far as the window 18. By means of the suction effect created in the area of the window 18, the tissue to be detached is sucked in through the window 18 and the opening 44. As the blade 51 of the cutting element 22 passes the blade 64 of the window 18, as can be seen from FIGS. 7 and 8, the suctioned tissue that is to be detached is then detached. The detached tissue 120 is sucked through the inner shaft 28 to the proximal end 13 of the instrument 10.

As will be apparent from FIGS. 6 to 8, each of the openings 44, 46, 48 has a smaller width than the window 18 of the outer shaft 12.

The webs 56, 58, 60 also have a smaller width than the window 18 of the outer shaft 12.

In this way, the window 18 of the outer shaft 12 always remains at least partially open, such that the suction effect created in the area of the window 18 is not interrupted in any position of rotation of the cutting element 22.

In a combination of the cutting element 22 with the outer shaft 12 that has only a single window 18, three cutting processes can take place during a complete revolution of the cutting element 22, with tissue fragments of appropriate size being detached in each case.

By combining the cutting element 70 with the outer shaft 92 that has three windows 96, 98, 100, a still greater cutting performance is achieved, particularly when tissue all the way round is to be detached.

What is claimed is:

1. A medical instrument for cutting tissue comprising
    a tubular outer shaft having in an area of its distal end a single window, said single window having at least one blade,
    a tubular inner shaft being rotatable about a longitudinal axis, that tubular inner shaft is received within said outer shaft, said tubular inner shaft having at a distal end thereof a cutting element which is arranged in an area of said single window of said outer shaft, an outer diameter of said tubular inner shaft corresponds to an inner diameter of said tubular outer shaft, said tubular inner shaft being adapted for connecting to a suction source,
    said cutting element having three circumferentially arranged openings, each of said three openings are holes in a wall of said inner shaft entirely passing through said wall, each of said openings of said cutting element having at least one blade which, when said cutting element is moved in rotation within said outer shaft, cooperates in a cutting action with said at least one blade of said outer shaft,
    wherein at least one of said three openings of said cutting element has the greatest width as seen in a respective circumferential direction of each of the openings and wherein at least one of said three openings of said cutting element has the smallest width as seen in a respective circumferential direction of each of the openings, resulting in openings of different size but same shape, and
    wherein said single window of said outer shaft, seen in a circumferential direction, is wider than a largest opening of said openings of said cutting element, said single window remains at least partially open when turning said tubular inner shaft,
    thereby a suction effect created by a suction source connected to said tubular inner shaft is not interrupted.

2. The medical instrument of claim 1, wherein said single window of said outer shaft has a same geometry as said three openings of said cutting element received in said outer shaft.

* * * * *